United States Patent [19]

Fischer

[11] 4,207,091

[45] Jun. 10, 1980

[54] METHOD OF PREVENTING PLANTS FROM DAMAGE BY FROST

[75] Inventor: Hanspeter Fischer, Bottmingen, Switzerland

[73] Assignee: Ciba-Geigy Corporation, Ardsley, N.Y.

[21] Appl. No.: 938,207

[22] Filed: Aug. 30, 1978

Related U.S. Application Data

[63] Continuation-in-part of Ser. No. 764,625, Feb. 1, 1977, abandoned.

[30] Foreign Application Priority Data

Feb. 9, 1976 [CH] Switzerland .................. 1522/76

[51] Int. Cl.² .......................................... A01N 9/24
[52] U.S. Cl. ............................... 71/113; 71/97; 71/118; 71/121
[58] Field of Search ................. 71/118, 113, 121, 97

[56] References Cited

U.S. PATENT DOCUMENTS

| | | | |
|---|---|---|---|
| 2,397,508 | 4/1946 | Roualt et al. | 260/500.5 H |
| 3,202,700 | 8/1965 | Kaczka et al. | 71/113 |
| 3,277,107 | 10/1966 | Neighbors | 71/118 |
| 3,539,373 | 11/1970 | Cooke | 71/DIG. 1 |
| 3,691,234 | 9/1972 | Kiefer et al. | 71/113 |
| 3,714,361 | 1/1973 | Morimoto et al. | 424/320 |
| 3,806,334 | 4/1974 | Hoegerle et al. | 71/113 |
| 3,914,300 | 10/1975 | Haddock et al. | 71/118 |
| 4,021,230 | 5/1977 | Cooke et al. | 71/111 |

FOREIGN PATENT DOCUMENTS 45-2375 1/1970 Japan ........................................ 71/113

OTHER PUBLICATIONS

Schoen et al., "Enzymatically Active Polyurethane, etc.," (1975), CA84, No. 1778f, (1976).
Hase et al., "Antimicrobial Activity, etc.," (1970), Chem. Pharm. Bull., pp. 363–368, (1971).
Leigh, "Pivalic Acid Derivatives," (1962), CA57, pp. 8444–8445, (1962).

*Primary Examiner*—Glennon H. Hollrah
*Attorney, Agent, or Firm*—Frederick H. Rabin

[57] ABSTRACT

The present invention provides a method of preventing plants, such as fruit, vegetables etc. from damage by frost. The method consists in treating the said plants, before outbreak of frost, with an effective amount of a hydroxamic acid derivative of formula

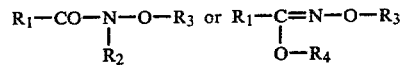

wherein
 $R_1$ is alkyl or cycloalkyl,
 $R_2$ represents hydrogen or the methyl group,
 $R_3$ is hydrogen, methyl, alkyl-carbonyl or a cation, and
 $R_4$ is hydrogen, methyl or ethyl.

10 Claims, No Drawings

METHOD OF PREVENTING PLANTS FROM DAMAGE BY FROST

CROSS REFERENCE TO RELATED APPLICATION

This is a continuation-in-part of my application, Ser. No. 764,625, filed Feb. 1, 1977 now abandoned.

DETAILED DESCRIPTION

The present invention provides a method of preventing plants, in particular plant cultures, such as fruit, vegetables, ornamentals including shrubs and trees, from damage by frost.

The prevention of frost damage to crops of cultivated plants is an extremely important problem in agriculture and horticulture. For this reason numerous active substances and measures have been proposed in order to increase the freeze resistance, that is to say the resistance of cultivated and ornamental plants to the action of cold and frost and in this way to prevent frost damage. Besides the application of polymers, foams and mists, the application in question is often of substances which constitute protectives against the destruction of the plant cells by freezing caused by damage to the membranes. Frost damage is frequently attributable to irreversible structural changes in the cell membranes and consequently of associated proteins, that is to say for example to changes in the permeability which result in the collapse of vital cell functions.

A large number of substances for protecting plant cells against destruction by freezing have been proposed, but most of them are not entirely satisfactory, because their application is restricted only to specific plants or because they induce phytotoxic side-effects or act as plant growth inhibitors (stunting agents) which is an undesired side effect.

It has also been proposed to use growth regulators which lower the metabolism of the plant and bring about a reduction of the vegetative growth and so maintain the plant in the dormant state, so that it becomes much less susceptible to frost.

Among the many frost protectives for plants, hydroxamic acids and the derivatives thereof have so far never been proposed.

The surprising discovery has now been made that hydroxamic acid derivatives of the formula I

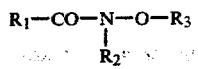
(I)

or of the "tautomeric" formula Ia

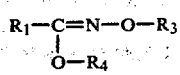
(Ia)

wherein
- $R_1$ represents a straight chain or branched $C_1$–$C_7$ alkyl group optionally substituted by chlorine, or a cycloalkyl group of 3 to 6 carbon atoms,
- $R_2$ represents a hydrogen atom or the methyl group,
- $R_3$ represents a hydrogen atom, the methyl group, an alkylcarbonyl group having 1 to 11 carbon atoms in the alkyl moiety, which may be a straight chain or branched, or the equivalent of a metal, amine or quaternary ammonio cation, and
- $R_4$ represents a hydrogen atom, the methyl or ethyl group, are exceptionally suitable as frost preventatives for cultivated plants, such as in particular fruit crops (citrus fruit, peaches, cherries, apples etc.), and also vegetables (beans and peas), and ornamentals including shrubs and trees.

Suitable metal cations $R_3$ are chiefly those of alkali metals and alkaline earth metals, and also those of trace elements, such as copper, iron and manganese.

The method of preventing frost damage of plants comprises treating the plants or parts of plants to be protected, before the onset of winter or before a suspected outbreak of frost, with an effective amount of a hydroxamic acid derivative of the formula I or Ia.

The active compounds of the formula I and Ia exert a substantial continuous preventive action which, on application in the autumn, lasts into the spring. The protective action occurs immediately, so that treatment on the day before an outbreak of frost guarantees satisfactory protection against frost damage.

Preferably, those compounds of the formula I are used in which $R_1$ represents the cyclopropyl group or an alkyl group of 1 to 4 carbon atoms, $R_2$ and $R_4$ represent hydrogen or methyl and $R_3$ represents hydrogen or one of the cations referred to, or the methyl group or a lower alkylcarbonyl group.

The majority of the active compounds of the formula I and Ia are known compounds and are described, for example, in Houben-Weyl, Vol. 8, pp. 684–692; Beilstein, Vol. 9, page 341 and in other literature sources. They are compounds which are stable and soluble in water and ordinary organic solvents.

A number of other hydroxamic acid derivatives have already been proposed as herbicides and fungicides and as growth stimulators in veterinary medicine (for example U.S. Pat. No. 3,714,361). In order to be usable as frost preventing agents, the active ingredients should not have phytotoxic side-effects and should show at most weak and preferably no stunting effect, i.e. should not cause any notable plant growth inhibiting action. The hydroxamic acid derivatives of formula I and Ia fulfil these conditions.

Some hydroxamic acid derivatives also exhibit plant growth-regulating properties, such as the promotion of fruit and leaf abscission.

Alkyl groups $R_1$ can be straight-chain or branched. A possible substituent of such alkyl groups is chlorine.

Active compounds which exemplify hydroxamic acid derivatives of the formula

(I)

are listed in the following table:

| Compound | $R_1$ | $R_2$ | $R_3$ | Physical constants m.p. in °C. |
|---|---|---|---|---|
| 1 | $CH_3(CH_2)_4-$ | H | H | 63°-65° |
| 2 | cyclohexyl | H | H | 130° |
| 3 | cyclohexyl | H | $K^\oplus$ | amorphous |
| 4 | tert. $C_4H_9$ | H | H | 167°-168° |
| 5 | n-$C_6H_{13}$ | H | H | 67°-69° |
| 6 | $CH_3(CH_2)_4-$ | H | $K^+$ | amorphous |
| 7 | n-$C_3H_7$ | H | H | 42° |
| 8 | n-$C_4H_9$ | H | H | |
| 9 | n-$C_7H_{15}$ | H | H | 79° |
| 10 | $CH_3(CH_2)_3-CH(CH_3)-$ | H | H | |
| 11 | tert. $C_4H_9$ | H | $HN^\oplus(C_2H_4OH)_3$ | |
| 12 | $(CH_3)_2CH-(CH_2)_3-$ | H | H | |
| 13 | cyclopentyl | H | H | |
| 14 | $Cl-(CH_2)_5-$ | H | H | |
| 15 | $CH_3(CH_2)_4-$ | $CH_3$ | $CH_3$ | |
| 16 | $CH_3(CH_2)_4-$ | H | $HN^\oplus[(CH_2)_2OH]_3$ | |
| 17 | $CH_3(CH_2)_4-$ | H | $HN^\oplus(C_2H_5)_3$ | |
| 18 | tert. $C_4H_9$ | H | $K^\oplus$ | >250° |
| 19 | tert. $C_4H_9$ | H | $-CO-CH_3$ | 114°-116° |
| 20 | n-$C_5H_{11}$ | $CH_3$ | $CH_3$ | $b.p._{11} = 96°$ |
| 21 | tert. $C_4H_9$ | $CH_3$ | $CH_3$ | $b.p._{12} = 62°$ |
| 22 | n-$C_5H_{11}$ | H | $-COCH_3$ | 76°-79° |
| 23 | tert. $C_4H_9$ | H | $\frac{1}{3} Fe^{+++}$ | >270° |
| 24 | iso-$C_3H_7$ | H | H | 116° |
| 25 | tert. $C_4H_9$ | H | $CH_3$ | $n_D^{20} = 1.4439$ |
| 26 | n-$C_4H_9$ | H | $-COCH_3$ | 62°-65° |
| 27 | $Cl-(CH_2)_3-$ | $CH_3$ | $CH_3$ | $b.p._{13} = 113°$ |
| 28 | cyclopropyl | H | $K^+$ | 114°-117° |
| 29 | cyclopropyl | H | H | 116° |
| 30 | tert. $C_4H_9$ | H | $-CO-$tert. $C_4H_9$ | 147°-148° |
| 31 | $CH_3(CH_2)_3-CH(C_2H_5)-$ | H | $\frac{1}{2} Cu^{++}$ | >200° |
| 32 | $CH_3$ | H | H | 87°-89° |
| 33 | $C_2H_5$ | H | H | 68°-69° |
| 34 | $ClCH_2-$ | H | H | 85°-90° |
| 35 | tert. $C_4H_9$ | H | $-CO-C_{11}H_{23}(n)$ | 36°-38° |
| 36 | n-$C_4H_9$ | H | H | |
| 37 | n-$C_3H_7-CH(CH_3)-$ | H | H | |
| 38 | iso-$C_4H_9$ | H | H | 72°-75° |
| 39 | n-$C_4H_9-CH(C_2H_5)-$ | H | H | |
| 40 | $(C_2H_5)_2CH-$ | H | H | |

Hydroxamic acid derivatives of the "tautomeric" formula $$R_1-C(=N-O-R_3)-O-R_4 \quad (Ia)$$

| Compound | $R_1$ | $R_3$ | $R_4$ | Physical constants |
|---|---|---|---|---|
| 41 | n-$C_5H_{11}$ | $CH_3$ | $CH_3$ | $b.p._{40} = 70°$ C. |
| 42 | $CH_3$ | H | $C_2H_5$ | m.p. 25°-26° C. |

It is preferable to apply the active ingredients in the form of compositions, i.e. together with suitable carriers and additives. These carriers and additives can be solid or liquid and correspond to the substances customarily used in the art of formulation, for example natural or regenerated mineral substances, solvents, dispersants, wetting agents, thickeners, binders or fertilisers.

For application, the compounds of the formula I or Ia can be formulated as follows:

Solid formulations: dusts, tracking agents, microgranules.

Liquid formulations:
 (a) water-dispersible active substance concentrates: wettable powders, pastes, emulsions;
 (b) solutions.

Solid formulations (dusts, tracking agents)

are obtained by mixing the active substances with solid carriers.

Water-dispersible concentrates, i.e. wettable powders, pastes and emulsifiable concentrates, are compositions which can be diluted with water to the desired concentration. They consist of active substance, carrier, optionally additives which stabilize the active substance, surfaceactive substances and anti-foam agents and, if appropriate, solvents.

Wettable powders and pastes are obtained by mixing and grinding the active substances with dispersing agents and pulverulent carriers in suitable devices until homogeneity is attained.

The active substance is so mixed, ground sieved and strained with the additives mentioned above that, in wettable powders, the solid particle size of 0.02 to 0.04 mm and in pastes, of 0.03 mm, is not exceeded. Emulsifiable concentrates and pastes are manufactured by using dispersing agents, organic solvents, and water.

Furthermore, the active ingredients can be applied in the form of solutions. For this purpose the active substances of the general formula I are dissolved in suitable organic solvents, mixtures of solvents or in water.

The above described compositions contain between 0.1 and 95%, preferably between 1 and 80%, of active compound. Application formulations can be diluted to the desired concentration of 500 ppm or 1000 ppm.

The use of the active compounds in the form of dusts, tracking agents, wettable powders and emulsifiable concentrates, as well as frost-resistant solutions and aerosols, is particularly preferred.

The compounds of the formula I and Ia which are absorbed by plants and not prematurely metabolised and effect no or only a slight growth inhibition without being noticeably phytotoxic, therefore best fulfil the expectations which can be placed in frost preventatives. The effective amounts to be applied vary depending on the plants to be treated and also on the derivative used. Normally, the plants or part of plants are sprayed with a spray broth until run-off. The concentration of the broth can vary between 100 and 8000 ppm and lies normally around 500–1000 ppm of active substance.

The protective action of the hydroxamic acid derivatives against frost was determined and evaluated by means of the following tests:

(1) Frost-resistant test on beans

Beam plants of the Felix variety were reared in a greenhouse in earthen-ware pots and sprayed with an aqueous preparation of the active compounds listed hereinafter at the commencement of flowering. The concentration of active compound in the spray broth was 1000 ppm. Eighteen plants were sprayed per treatment. Untreated plants were used as controls. Seven days after the application the test plants were placed in a climatic chamber, the temperature was slowly lowered to −1° C., kept thereat for a brief time, and thereafter slowly raised again to room temperature. Evaluation was made 10 days after this cold treatment and each plant was inspected for frost damage using the following evaluation scale:

| | | |
|---|---|---|
| − | = | all plants withered (as control) |
| (+) | = | slight frost damage prevention |
| + | = | good frost damage prevention |
| ++ | = | very good frost damage prevention |
| +++ | = | all plants without any trace of frost damage. |

-continued

| Results Compound No. | Frost-protective action |
|---|---|
| 1 | (+) |
| 3 | (+) |
| 4 | ++ |
| 5 | + |
| 6 | + |
| 19 | + |
| 22 | + |
| 25 | (+) |
| 26 | ++ |
| 27 | (+) |
| 28 | + |
| 29 | ++ |
| 30 | + |

In another test the bean plants were treated twice with a preparation of compound 1, namely (a) twice at a concentration of 100 ppm and (b) twice at a concentration of 500 ppm. One week after the second treatment, the plants were exposed for 1 hour to a temperature of −4° C. and then restored to normal conditions.

The test was evaluated one week later. Whereas the damage to untreated bean plants was 100%, i.e. total, the frost damage to plants treated with the said active substance at a concentration of 100 ppm was 40% and only 15% to plants treated with this active substance at a concentration of 500 ppm.

(2) Frost-resistant test on citrus plants

Citrus trees were treated with compound 1 in the concentrations indicated below one day before a frost predicted in a weather forecast. In the following night the temperature fell for 4 to 5 hours to −3° C. Six days later the following results of the damage caused could be determined:

| | Treatment with spray broth concentration | Hamlin oranges and Valencia oranges % age damage to | | |
|---|---|---|---|---|
| Compound 1 | in ppm | old leaves | new leaves | blossoms |
| | 500 | 0 | 80 | 60 |
| | 1000 | 0 | 70 | 60 |
| | 1500 | 0 | 70 | 60 |
| | untreated | 0 | 90 | 90 |

(3) Frost-resistant tests in fruit cultures (a) For these tests, devices (cages) were used which make it possible to produce frost conditions on individual branches of a pear tree. Compound 1 was sprayed on blossombearing branches of pear trees at a time when the blossoms were just on the point of opening, viz. at the time of the greatest susceptibility to frost. Some days after this spray treatment, "cages" were placed over the treated and untreated branches of the same tree and then, at night, a frost with a minimum temperature of −3° C. was artificially produced in these cages. A few days later the frost damage to the blossoms was determined by microscopic examination and the following results were obtained:

treatment with 2000 ppm of compound 1=74% damage
treatment with 4000 ppm of compound 1=26% damage
untreated branches=97% damage (b) Peach trees were sprayed in the autumn with a liquid preparation of compound 1 just as the leaves were beginning to turn in colour and wither. In January, branches were collected and subjected for 24 hours to a cold treatment in the course of which the temperature was lowered stepwise by 2° C. an hour to a minimum temperature of −21° C. and then raised again. The microscopic examination of many buds (embryos) was made two days later in order to ascertain how many had perished and how many had survived.

| Result | % age of surviving buds |
| --- | --- |
| treatment with 1000 ppm | 74% |
| treatment with 2000 ppm | 83% |
| treatment with 8000 ppm | 88% |
| untreated | 63% |

(4) Frost-resistant test on peas

Seeds of peas (variety "gloire du midi") were sown in seed dishes of 60×40 cm, filled with earth. Each dish contained 64 seeds. 14 days after sowing, when the emerged pea plants had reached about 15–20 cm height, one half of the plants (32) in each dish were treated with an aqueous spray broth of a concentration of 1000 ppm of active ingredients listed hereinafter, until run-off. The other 32 plants of each dish were left untreated and served as controls. Seven days after treatment, all test plants were placed in a climatic chamber and the temperature was slowly lowered to −5° C. and kept thereat for 14 hours (over night). Thereafter, the temperature was slowly raised again to room temperature. Evaluation of the results was made 8 days after this cold treatment either by visual bonification and expressing the result by using the same evaluation scale as in test 1 (with beans), or by determination of the fresh weight of the untreated and treated plants of each dish.

| Results | |
| --- | --- |
| (a) visual bonification | |
| Compound | frost protective action |
| 2 | + |
| 3 | + |
| 4 | ++ |
| 6 | + |
| 7 | + |
| 11 | + |
| 18 | ++ |
| 19 | + |
| 21 | (+) |
| 22 | + |
| 23 | + |
| 24 | + |
| 25 | (+) |
| 28 | ++ |
| 29 | ++ |
| 30 | + |
| 31 | + |
| 32 | ++ |
| 33 | (+) |
| 34 | + |
| 35 | + |
| 38 | (+) |
| 41 | (+) |
| 42 | + |

| (b) determination of the fresh weights (for some elected test compounds) | |
| --- | --- |
| Compound No. | increase of the fresh weight of pea plants treated with spray broth, with respect to the untreated plants damaged by the frost, after 8 days |
| 4 | + 39% |
| 18 | + 56% |
| 32 | + 64% |

I claim:
1. A method of preventing frost damage on plants which comprises applying to the plant or to parts of the plants to be protected against frost damage, before the onset of winter or before a suspected outbreak of frost, an effective amount of a hydroxamic acid derivative of the formula

or of the "tautomeric" formula

wherein
$R_1$ is a straight-chain or branched $C_1$-$C_7$ alkyl group optionally substituted by chlorine, or a $C_3$-$C_6$ cycloalkyl group,
$R_2$ is hydrogen or the methyl group,
$R_3$ is hydrogen, the methyl group, an alkylcarbonyl group in which the straight-chain or branched alkyl moiety has from 1 to 11 carbon atoms, or is an equivalent of a metal selected from the group consisting of alkali metals, alkaline earth metals, manganese, iron and copper, or an amine or quaternary ammonio cation, and
$R_4$ is hydrogen, the methyl or ethyl group.
2. The method according to claim 1 for protecting cultures of fruit, vegetable and ornamentals.
3. The method according to claim 1 wherein in the compound employed of formula I or Ia $R_1$ is a straight-chain or branched $C_1$-$C_4$ alkyl group or the cyclopropyl group, each of $R_2$ and $R_4$ is hydrogen or methyl and $R_3$ is hydrogen, an alkali metal cation or a lower alkylcarbonyl group.
4. The method according to claim 3 wherein the compound employed is n-pentanecarbohydroxamic acid of the formula

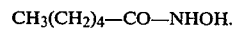

5. The method according to claim 3 wherein the compound employed is 2-methyl-propane-2-carbohydroxamic acid of the formula

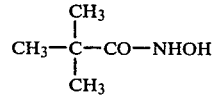

6. The method according to claim 3 wherein the compound employed is the potassium salt of 2-methyl-propane-2-carbohydroxamic acid of the formula

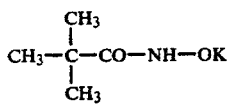

7. The method according to claim 3 wherein the compound employed is methanecarbohydroxamic acid of the formula

CH₃—CO—NHOH

8. The method according to claim 3 wherein the compound employed is 2-methylpropane-2-carbohydroxamic acetate of the formula

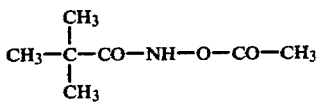

9. The method according to claim 3 wherein the compound employed is cyclopropane carbohydroxamic acid of the formula

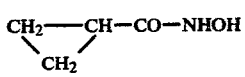

or its potassium salt.

10. The method according to claim 3 wherein the compound employed is n-butanecarbohydroxamic acetate of the formula

CH₃(CH₂)₃—CO—NH—O—CO—CH₃.

* * * * *